United States Patent [19]

Engelmann

[11] Plant 4,516

[45] Apr. 1, 1980

[54] ACANTHUS FAMILY

[76] Inventor: Hermann H. Engelmann, P.O. Box 1227, Apopka, Fla. 32703

[21] Appl. No.: 963,835

[22] Filed: Nov. 27, 1978

[51] Int. Cl.[2] ..... A01H 5/00

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new plant variety of the Acanthus family is related to the *Fittonia Verschaffeltii* argyroneura 'Minima' and has comparably sized plant parts but is distinguished therefrom primarily by a variegated leaf blade that has a basic chlorophyllous field that is lighter than the chlorophyllous field of the parent 'Minima' variety.

2 Drawing Figures

This invention relates to a new and distinct plant variety of the Acanthus family and which has been developed from a sport or bud variation that appeared on a plant specimen of the *Fittonia Verschaffeltii* argyroneura 'Minima' variety. The specimen was under cultivation in a nursery in the vicinity of Apopka, Fla. at the time of the discovery and since then, the new variety has been asexually reproduced at the same nursery and by the propagation of stem cuttings taken from the specimen.

Plant specimens of the 'Minima' variety are related to the plant specimens of the *Fittonia Verschaffeltii* argyroneura 'Nerve plant' variety. Both of these varieties are characterized by a mosaic leaf venation pattern in a leaf blade that has a basic chlorophyllous field which is solid except for the discontinuities along the veins of the blade. In both varieties the color of the basic field is generally darker than the basic chlorophyllous field of the new variety and the principle characteristic that distinguishes the 'Minima' and the 'Nerve plant' varieties is the fact that the former is substantially smaller in size than the latter.

One object of the invention has been to develop a new variety of the Acanthus family for the foliage plant market and which is distinguishable from the known varieties of this family. This object has been fully realized by the invention as will be apparent from the following plant description contained herein and where it will be seen that the new plant variety is distinguishable from its antecedents and known related varieties by a growth habit that provides specimens which have plant parts that, in size, closely approach those of the 'Minima' variety and which have a variegated leaf blade with the mosaic leaf venation pattern that is characteristic of the 'Nerve plant' and 'Minima' varieties and a basic chlorophyllous field that in color is visibly lighter than the basic fields of the 'Minima' and 'Nerve plant' variety and normally dominated by a yellow green hue, the variegated leaf blade being in particular distinguishable by marginally located achlorophyllous blotches or specks.

The accompanying drawing serve by color photographic means to illustrate the new variety, one sheet showing a single plant specimen of the new variety while the other sheet provides a photographic close-up of the leaf blades of the new variety.

The following is a detailed description of the new variety and is based on observations of well fertilized specimens which were grown in the central Florida area under approximately 80 percent shaded nursery conditions and where temperatures are generally maintained in the range from about 18° C. to about 30° C. during the winter months and from about 24° C. to about 36° C. during the summer months. The description is further based on the observations of specimens that were 5–8 months in age as measured from propagation.

Except where general terms of ordinary dictionary significance are obviously used, color terminology and color designations reported herein are in accord with the ISCC-NBS Method of Designating Colors as described in the U.S. Department of Commerce, National Bureau of Standards, Circular 553, entitled ISCC-NBS "Method of Designating Colors and Dictionary of Colored Terms" with the color designations having been derived through interpretation of Munsell Color Notations obtained by comparing plant specimens with the color specimens in the current "Neighboring Hues Edition" of The Munsell Book of Color, published by Munsell Color Company, Inc. of Baltimore, Md., and to which the reported notations (Munsell Hue, Munsell Value/Munsell Chroma) are referenced.

PLANT DESCRIPTION

Name: *Fittonia Verschaffeltii* argyroneura 'Angel Snow'.

Origin: Bud variation or a sport that appeared on a specimen of the variety known as *Fittonia Verschaffeltii* argyroneura 'Minima'.

Classification:

A. *Botanic.*—*Fittonia Verschaffeltii* var. argyroneura E. Coem. Acanthus family (Acanthaceae).

B. *Commercial.*—Foliage plant.

Form: Herbaceous, tropical perennial evergreen with adventitious root system.

Stem:

A. *General.*—Caulescent and ascending with decumbent tendencies and occasional axillary branching at the nodes.

B. *Surface.* —(1) General: Scarred and pubescent with hyaline vestiture and four circumferentially spaced apart and longitudinally extending continuous linear rows of hair. (2) Vestiture: Sericeous with strigose tendencies. (3) Row hairs: Velutinous, erect and colorless.

C. *Texture.*—Fleshy.

D. *Shape.*—Terete.

E. *Size.*—(1) Diameter: Commonly 1.5-3.0 mm. intermediate nodes at maturity. (2) Internode length: Commonly 0.5-2.5 cm. between fully developed nodes in mature specimens and usually shortening distally of the ground insertion.

F. *Color.*—(1) General: Generally uniform epidermal color with occasional variation from one stem to the next. (2) Epidermis: Commonly moderate yellow green (5 GY 7/6) (5 GY 6/6) (7.5 GY 7/6) (7.5 GY 6/6).

Leaves:

A. *General.*—Simple, incomplete, petiolate and extipulate. (1) Arrangement: Decussate. (2) Shape: (a) General — Generally symmetrical and ovate with occasional elliptical tendencies. (b) Leaf apices — Usually obtuse to broadly rounded with occasional acute tendencies. (c) Leaf Bases — Usually weakly cordate and occasionally showing truncate, oblique and obtuse tendencies. (d) Margins — Entire and ciliate with undulate tendencies. (e) Posture — 1. Transverse: Recurved. 2. Longitudinal: Revolute.

B. *Petioles.*—(1) Surface: (a) General — Pubescent with hyaline vestiture and three circumferentially spaced apart and longitudinally extending continuous linear rows of hairs that merge at the petiole insertion with the adjacent rows on the stems. (b) Vestiture — Sericeous with strigose tendencies. (c) Row hairs — Velutinous, erect and colorless. (2) Texture: Fleshy. (3) Shape: Elongated and generally obovate to depressed obovate in cross section. (4) Size: (a) Diameter—Commonly 0.5-2 mm. intermediate insertion and blades at maturity. (b) Length (insertion to blade base) — Commonly 7-20 mm. for mature leaves. (5) Color: (a) General — Concolorous with stem. (b) Commonly moderate yellow green (5 GY 7/6) (5 GY 6/6) (7.5 GY 7/6) (7.5 GY 6/6).

C. *Venation.*—(1) General: Reticulate and pinnate with camptodromous tendencies, the midrib and lateral secondary veins being variously interconnected by lateral tertiary veins. (2) Surface: (a) Upper epidermis — 1. Midrib: [a] General — Pubescent with hyaline vestiture and proximally located scattered velutinous hairs. [b] Vestiture — Sericeous and colorless. 2. Lateral veins: [a] General — Pubescent with hyaline vestiture. [b] Vestiture — Tomentose and colorless. (b) Lower epidermis — 1. Midrib: [a] General — Pubescent with hyaline vestiture and proximally located linear rows of velutinous, erect hairs that merge with the rows of hairs on the abaxial side of petiole. [b] Vestiture — Sericeous. 2. Lateral veins: [a] General — Glaucous and pubescent with hyaline vestiture. [b] Vestiture — Strigose and colorless with sericeous tendencies. (3) Texture: Fleshy. (4) Shape: (a) Midrib — Distally tapering and semiterete in cross section with the flattened surface being adaxially located so that the midrib is prominantly keeled at the abaxial side of the blade. (b) Lateral veins — 1. Secondary veins: Distally tapering and semiterete in cross section with the flattened surface being adaxially located so that the secondary veins are prominently keeled at the abaxial side of the blade. 2. Tertiary veins: Faintly ridged at abaxial side of blade. (5) Vein number: (a) Secondary veins — Usually 5-9 at each side of midrib. (b) Tertiary veins — Numerous. (6) Color: (a) Midrib — 1. General: Concolorous with petiole at base of midrib and becoming achlorophyllous distally thereof. 2. Adaxial side: Commonly moderate yellow green (5 GY 7/6) (5 GY 6/6) (7.5 GY 7/6) (7.5 GY 6/6) at proximal end and pale yellow green (10 Y 9/2), yellowish white (10 Y 9/1) and/or white (near 7.5 Y 9.5/0) at distal end. 3. Abaxial side: Same as adaxial side. (b) Lateral veins — Usually achlorophyllous on adaxial and abaxial sides and commonly yellowish white (10 Y 9/1) and/or white (near 7.5 Y 9.5/0).

D. *Leaf blades.*—(1) General: Chartaceous between veins. (2) Surface: (a) Upper epidermis — Scabrous and puberulent. (b) Lower epidermis — Glaucous, verruculose and sparingly strigose. (3) Texture: Chartaceous. (4) Size: (a) Length — Usually 2.5-5 cm. at maturity. (b) Width (maximum) — Usually 1.5-3 cm. at maturity. (5) Color: (a) General — Variegated upper epidermis with a basic chlorophyllous field that in color is normally dominated by a yellow green hue and occasionally shows reversionary tendencies, with marginally located irregular achlorophyllous blotches and/or flecks that are usually bounded on one or more sides by lateral leaf veins, the colors and patterns being somewhat obscured at the abaxial blade side by the translucent and glaucous nature of the lower epidermis. (b) Basic chlorophyllous field — Normally moderate yellow green (5 GY 5/6) (5 GY 6/6) (5 GY 7/6) (5 GY 6/4) (7.5 GY 5/6) (7.5 GY 6/6) (7.5 GY 5/4), strong yellow green (5 GY 6/8) (5 GY 7/8) and/or grayish yellow green (7.5 GY 5/2) with moderate olive green (7.5 GY 3/4) (7.5 GY 4/4), dark grayish green (10 GY 3/4) and/or dark yellowish green (10 GY 4/4) in reversional area occurrences. (c) Achlorophyllous blotches and flecks — Commonly pale yellow (5 Y 9/4) (near 7.5 Y 9/2), light yellow (5 Y 9/6), yellowish white (5 Y 9/2) (near 7.5 Y 9/2), light greenish yellow (7.5 Y 9/6) (near 10 Y 8/6), pale greenish yellow (7.5 Y 9/4) (near 10 Y 9/4), moderate greenish yellow (10 Y 8/6), pale yellow green (10 Y 9/2) (2.5 GY 9/2) (5 GY 9/2) and/or light yellow green (2.5 GY 8/6) (2.5 GY 9/6) (2.5 GY 9/4) (5 GY 9/4) (5 GY 8/6) (5 GY 8/4).

Inflorescences: None have been known to appear since discovery of the variety.

The following is a general description of a specimen of the new plant variety which was grown in a nursery at Apopka, Fla. from a single cutting having two nodes set horizontal in an industrial standard 2½ inch growing pot, the description being taken in August.

Age of specimen: 5 months from propagation.

Number of ascending stems: 8.

A. *Stems.*—(1) Diameter — Varies from about 2.0 to 2.5 mm. (2) Internode length — Varies between 1.0 and 2.0 cm. (3) Epidermis color — Moderate yellow green (5 GY 7/6) (5 GY 6/6).

B. *Leaves.*—(1) Petioles — (a) Diameter: Varies between 1 and 2 mm. (b) Length: Varies between 12 and 17 mm. (c) Color: Moderate yellow green (5 GY 7/6) (7.5 GY 7/6). (2) veins — (a) Midrib color: Moderate yellow green (5 GY 7/6) (5 GY 6/6) (7.5 GY 7/6) near petiole and pale yellow green (10 Y 9/2), and yellowish white (10 Y 9/1) at distal end. (b) Lateral vein number: 6–7 secondary veins at each side of midrib and spaced apart at 5–7 mm. intervals with tertiary veins being spaced apart in the range of about 1.5–4 mm. (c) Lateral vein color: Yellowish white (10 Y 9/1) (3) Leaf blades — (a) Length: 2.5–4 cm. (b) Width (maximum): 2.0–2.5 cm. (c) Color: 1. Basic chlorophyllous field — Moderate yellow green (5 GY 5/6) (5 GY 6/6) (7.5 GY 5/6) and strong yellow green (5 GY 6/8). 2. Achlorophyllous blotches and flecks — Light yellow (5 Y 9/6), yellowish white (5 Y 9/2), light greenish yellow (7.5 Y 9/6), moderate greenish yellow (10 Y 8/6) and light yellow green (2.5 GY 9/4) (5 GY 9/4).

I claim:

1. The new and distinct variety of the Acanthus family substantially as herein shown and described.

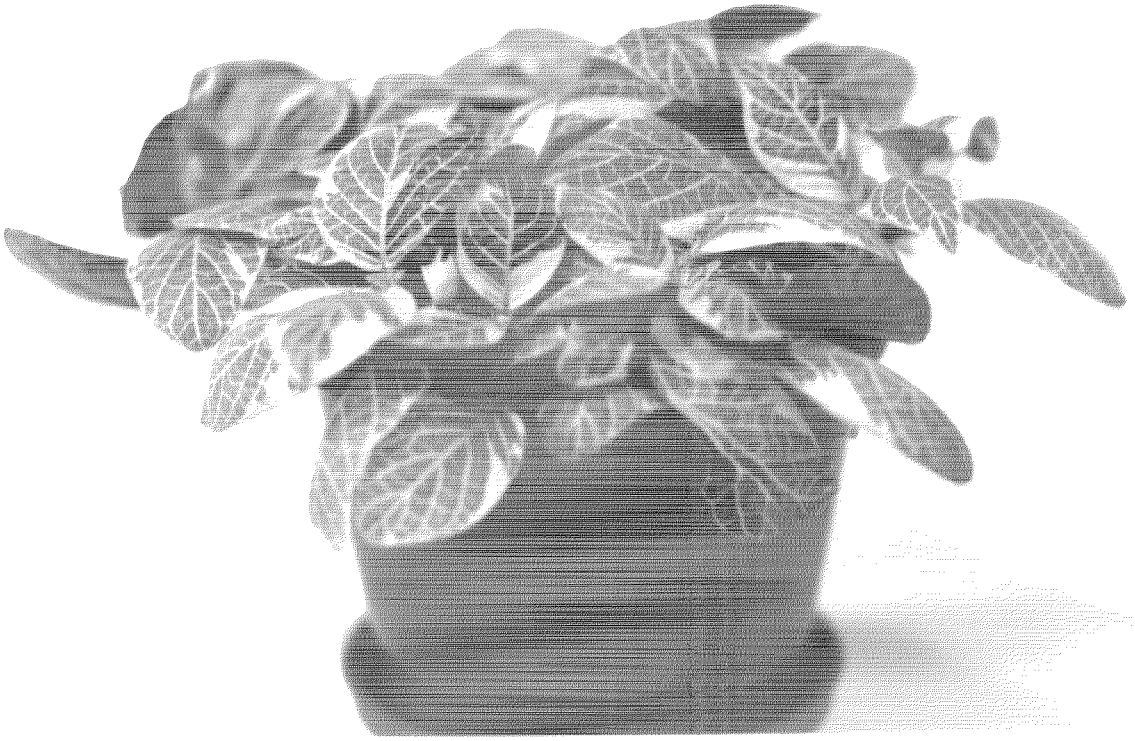

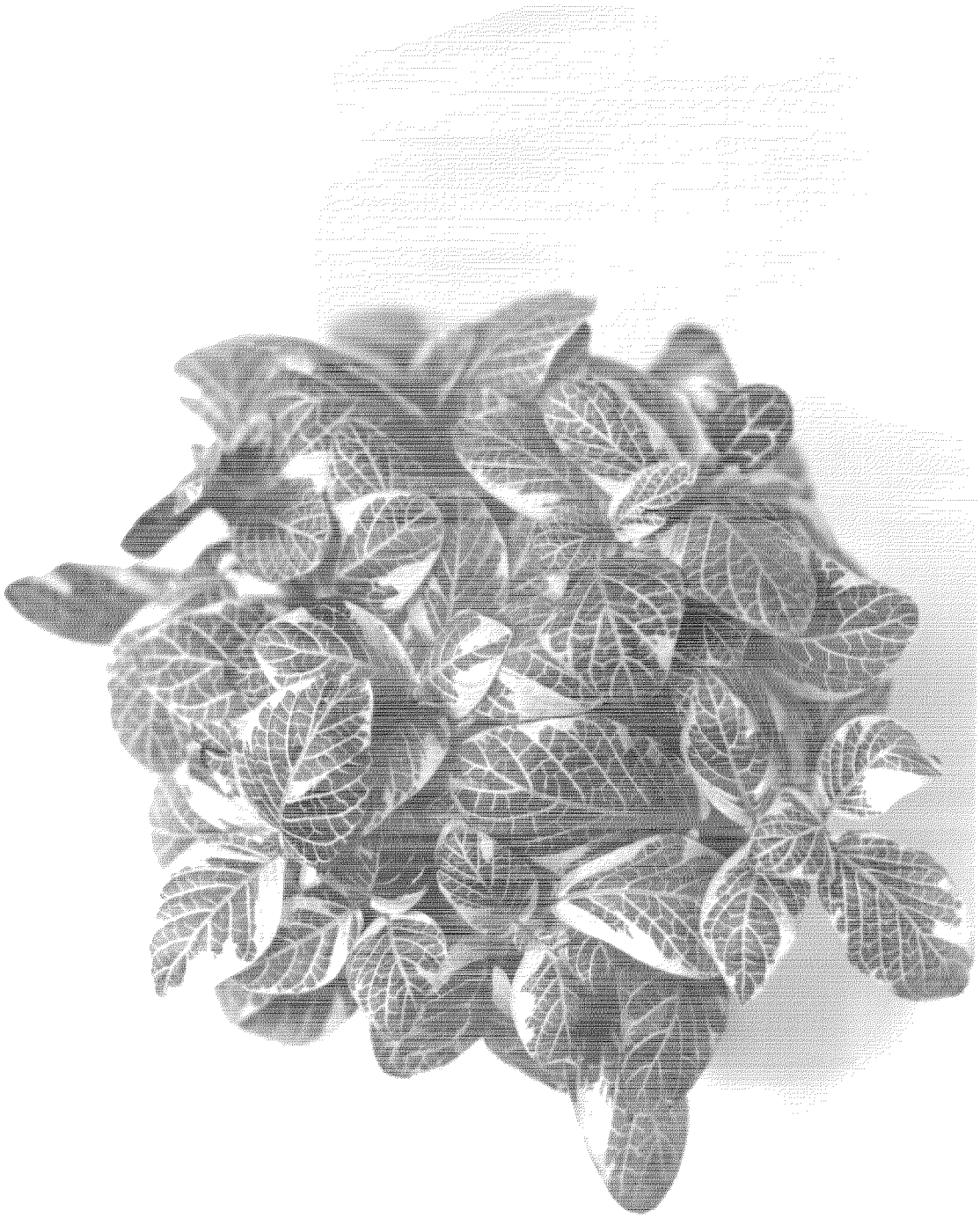

* * * * *